(12) United States Patent
Lai et al.

(10) Patent No.: US 6,382,794 B1
(45) Date of Patent: May 7, 2002

(54) METHOD AND APPARATUS FOR MAPPING A CORNEAL CONTOUR AND THICKNESS PROFILE

(75) Inventors: Ming Lai, Dublin; Barry T. Kavoussi, Danville; Christopher J. R. V. Baker, Moraga, all of CA (US)

(73) Assignee: Carl Zeiss, Inc., Thornwood, NY (US)

( * ) Notice: Subject to any disclaimer, the term of this patent is extended or adjusted under 35 U.S.C. 154(b) by 0 days.

(21) Appl. No.: 09/406,034

(22) Filed: Sep. 27, 1999

(51) Int. Cl.$^7$ .................................................. A61B 3/10
(52) U.S. Cl. ....................................................... 351/212
(58) Field of Search ................................. 351/205, 206, 351/208, 210, 211, 212, 214, 219, 221, 246; 606/4, 5, 166

(56) References Cited

U.S. PATENT DOCUMENTS

| | | | |
|---|---|---|---|
| 5,307,097 A | 4/1994 | Baker | 351/212 |
| 5,404,884 A | 4/1995 | Lempert | 128/665 |
| 5,512,965 A | 4/1996 | Snook | 351/205 |
| 5,512,966 A | 4/1996 | Snook | 351/205 |
| 5,592,246 A | 1/1997 | Kuhn et al. | 351/212 |
| 5,663,781 A | 9/1997 | Wilms et al. | 351/206 |
| 5,838,811 A | 11/1998 | Lindmark | 382/100 |
| 5,861,955 A | 1/1999 | Gordon | 356/360 |
| 5,864,382 A | 1/1999 | Soya et al. | 351/206 |
| 5,870,167 A | 2/1999 | Knopp et al. | 351/212 |
| 6,193,371 B1 * | 2/2001 | Snook | 351/212 |

* cited by examiner

*Primary Examiner*—George Manuel
(74) *Attorney, Agent, or Firm*—Michael B. Einschlag

(57) ABSTRACT

Method and apparatus is disclosed for mapping a corneal contour and thickness profile. In accordance with one aspect of the present invention, a set of narrow, collimated, parallel beams is projected onto a corneal surface at an angle with respect to a predetermined axis ("an instrument axis") that is substantially aligned with a visual axis of an eye. The set of beams is rotated about the instrument axis. A CCD camera is disposed to view the cornea along the instrument axis. Traces of the rotating set of beams form a set of rings in images obtained by the CCD camera; wherein outer and inner edges of the rings correspond to intersections of the set of beams with anterior and posterior surfaces of the cornea, respectively. Next, a direct triangulation algorithm is used to determine spatial positions of data points along the outer edges of the rings, and these spatial positions are used to reconstruct the anterior surface profile of the cornea. Next, using the anterior surface profile of the cornea, a ray tracing triangulation algorithm is used to determine spatial positions of data points along the inner edges of the rings, and these spatial positions are used to reconstruct the posterior surface profile of the cornea. Finally, spatial differences between the posterior and anterior surface profiles of the cornea provide the thickness profile.

25 Claims, 5 Drawing Sheets

METHOD AND APPARATUS FOR MAPPING A CORNEAL CONTOUR AND THICKNESS PROFILE

TECHNICAL FIELD OF THE INVENTION

The present invention pertains to optical analysis of a cornea. In particular, the present invention pertains to a method and apparatus for mapping a corneal contour and thickness profile.

BACKGROUND OF THE INVENTION

Accurate measurement of a corneal contour and thickness profile is important for photo-refractive surgery. These data are important to ensure surgical accuracy and documentation. For laser-in-situ-keratomileusis ("LASIK") in particular, such data are essential to ensure proper surgical decision making and to ensure safety.

It is well known in the art that corneal topography provides curvature information relating to the anterior corneal surface. However, in practice, this information alone does not provide enough information for a surgeon to determine whether a LASIK surgical procedure can be performed safely and effectively.

It is also well known in the art that Scheimpflug slit lamp photography can be used to investigate the cornea and anterior chamber of an eye. U.S. Pat. Nos. 5,512,965 and 5,512,966 of inventor Richard K. Snook ("the Snook patents") disclose a method and apparatus for measuring a corneal contour and thickness profile based on digitized slit lamp photography. In accordance with the Snook patents, a slit of light from an incandescent lamp is scanned over a cornea being examined to record a sequence of slit light images of the cornea with a CCD camera. The images are stored in a digital format and are analyzed to reconstruct the corneal contour and thickness profile. Further, a device referred to as an ORBSCAN II® slit-scan based, corneal and anterior segment topography system has been developed and manufactured by Orbtek, Inc. of Salt Lake City, Utah (now a part of Bausch & Lomb) based upon the disclosure of the Snook patents. The ORBSCAN II system device provides corneal information such as, for example, an elevation map, a curvature map, a power map, and a thickness (pachymetry) map.

One limitation of the method and apparatus disclosed in the Snook patents is the use of conventional slit lamp based technology. One limitation of conventional slit lamp based technology is that the slit lamp beam projects a focused beam with a rather short confocal length. As a result, the slit lamp image is not always sharp across the corneal surface. A further limitation of the slit lamp based technology is that only one slit image can be taken in each frame of a picture, and some forty (40) frames of pictures are required to achieve the required resolution. As a result, the sampling time is as long as a few seconds and patient eye movement becomes an issue. A yet further limitation of the slit lamp based technology is that a viewing angle along a slit lamp image varies from point to point. As a result, an algorithm used to reconstruct the corneal contour is rather complicated.

As a result, a need exists in the art for a method and apparatus for mapping a corneal contour and thickness profile that overcome the above-identified limitations of the slit lamp based technology.

SUMMARY OF THE INVENTION

Embodiments of the present invention advantageously provide method and apparatus for mapping a corneal contour and thickness profile that overcome the above-identified limitations of the slit lamp based technology. In accordance with one aspect of the present invention, an apparatus for mapping a corneal contour and thickness profile of a patient's eye comprises: (a) a source which projects a set of beams of radiation onto a cornea of the patient's eye; (b) a rotator which rotates the source; (c) a camera which acquires images of radiation scattered by the cornea; and (d) a controller that analyzes the images to construct the corneal contour and thickness profile.

In particular, in accordance with a preferred embodiment of the first aspect of the present invention, a set of beams of radiation is projected onto a corneal surface at an angle with respect to a predetermined axis ("an instrument axis"). In operation, the instrument axis is substantially aligned with a visual axis of an eye, and the set of beams is rotated about the instrument axis. A camera (for example, a CCD camera) is disposed to view the cornea along the instrument axis. Since corneal stroma scatter the radiation more strongly than does the aqueous humor of the anterior chamber of the eye, traces of the rotating set of beams form a set of rings in images obtained by the camera. The outer and inner edges of the rings correspond to intersections of the set of beams with anterior and posterior surfaces of the cornea, respectively. Then, in accordance with the present invention, a direct triangulation algorithm is used to determine spatial positions of data points along the outer edges of the rings. These spatial positions are then used to reconstruct the anterior surface profile of the cornea. Next, using the anterior surface profile of the cornea, a ray tracing triangulation algorithm is used to determine spatial positions of data points along the inner edges of the rings. Next, these later spatial positions are used to reconstruct the posterior surface profile of the cornea. Finally, spatial differences between the posterior and anterior surface profiles of the cornea are used to generate the thickness profile. Advantageously, in comparison with the prior art technology, embodiments of the present invention provide: (a) a sharper beam image; (b) more data points for each frame of a camera image; and (c) a simpler algorithm for mapping the corneal contour and thickness profile.

In accordance with a second aspect of the present invention, an apparatus for mapping a corneal contour and thickness profile of a patient's eye comprises: (a) a source which projects a beam of radiation onto a cornea of the patient's eye; (b) a rotator which rotates the source; (c) a displacement mechanism which displaces the source; (d) a camera which acquires images of radiation scattered by the cornea at various displacements of the source; and (e) a controller which analyzes the images to construct the corneal contour and thickness profile.

In particular, in accordance with a preferred embodiment of the second aspect of the present invention, a single beam of non-coherent radiation is projected onto a corneal surface at an angle with respect to a predetermined axis ("an instrument axis"). In operation, the instrument axis is substantially aligned with a visual axis of an eye, and the beam is rotated about the instrument axis. A camera (for example, a CCD camera) is disposed to view the cornea along the instrument axis using near confocal configuration. The beam is displaced slightly for each rotation and the camera acquires a series of images of rings which are analyzed as discussed above. In accordance with this embodiment, when the beam is displaced, an optical focusing system can also be displaced to maintain near confocal imaging.

DETAILED DESCRIPTION

Figure 1:
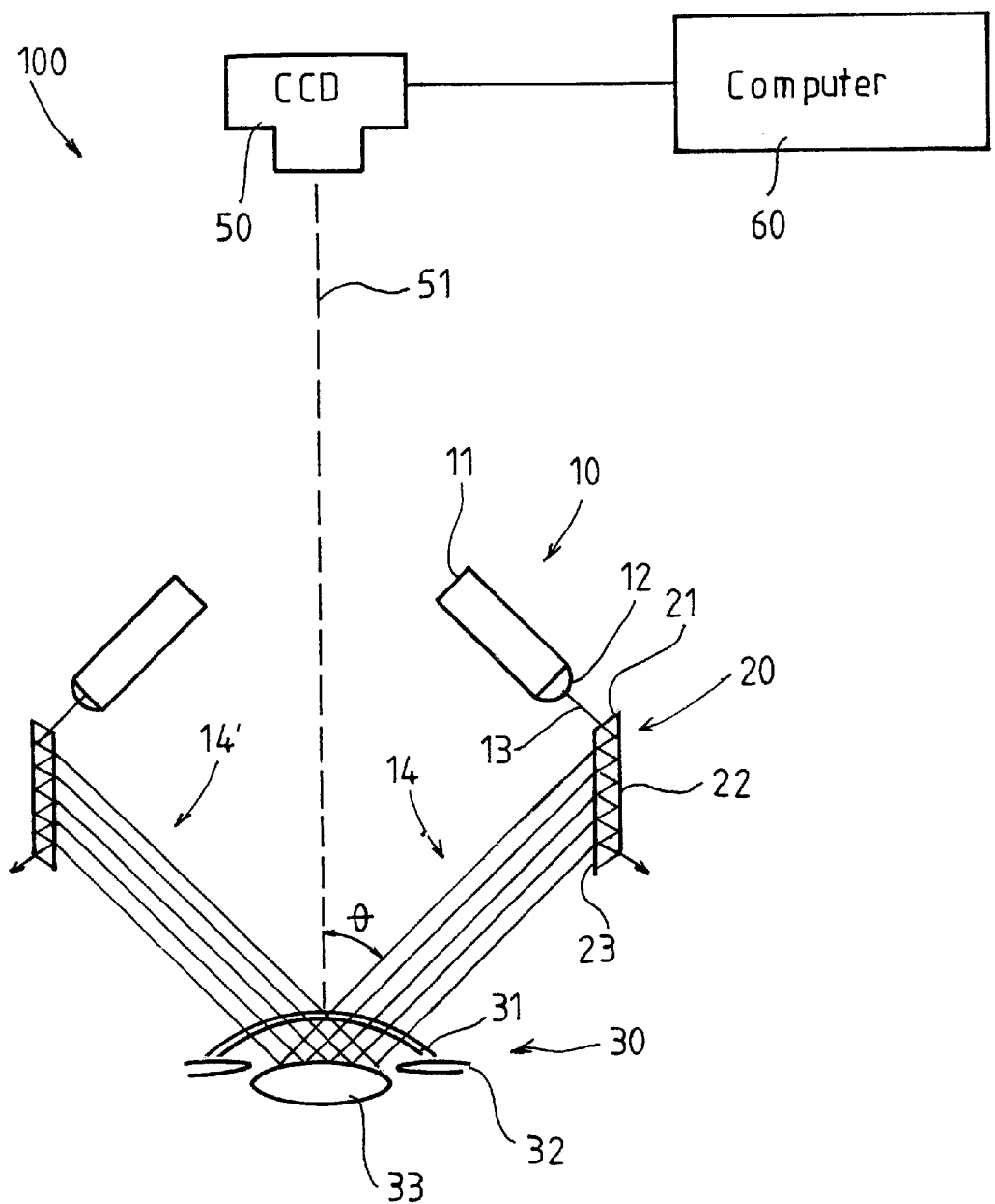
FIG. 1 shows, in pictorial form, an embodiment of the present invention used for mapping a corneal contour and thickness profile.

FIG. 1 shows, in pictorial form, embodiment 100 of the present invention used for mapping a corneal contour and thickness profile. As shown in FIG. 1, radiation assembly 10 comprises diode laser head 11 and focal lens system 12. Radiation assembly 10 produces, as output, beam of radiation 13 which is preferably an infrared beam of radiation (in a preferred embodiment, the radiation has a wavelength substantially in a range from about 700 nm to about 1300 nm). The focal distance and pointing direction of beam of radiation 13 are adjusted using any one of a number of mechanisms that are well known to those of ordinary skill in the art, which mechanism is not shown for ease of understanding the principles of operation of the present invention. Although radiation assembly 10 outputs infrared radiation, the present invention is not limited thereto. However, infrared radiation is preferred since, as is well known in the art, a patient will not perceive the presence of infrared radiation.

As further shown in FIG. 1, beam of radiation 13 is directed to impinge upon optical plate 20 through surface 21. In accordance with the present invention, surface 22 of optical plate 20 is coated with a high reflection coating for radiation comprising beam of radiation 13, and surface 23 is coated with a partially reflecting coating for radiation comprising beam of radiation 13. Many methods and coatings for fabricating optical plate 20 are well known to those of ordinary skill in the art.

As still further shown in FIG. 1, radiation in beam of radiation 13 reflects back and forth between surfaces 22 and 23 of optical plate 20. As a result, and in accordance with the present invention, a set of substantially parallel beams of radiation 14 is generated wherein beams comprising set of beams of radiation 14 are separated; in a preferred embodiment, the beams are separated by substantially equal amounts. In accordance with a preferred embodiment of the present invention, surface 21 is cut: (a) to receive beam of radiation 13 at Brewster's angle to minimize reflective loss or (b) to provide normal incidence of beam of radiation 13 to provide simple alignment of embodiment 100.

As shown in FIG. 1, substantially parallel set of beams of radiation 14 are projected onto cornea 31 of patient's eye 30 at a predetermined angle θ0 with respect to instrument axis 51 of embodiment 100. As further shown in FIG. 1, a second, identical set of parallel beams of radiation 14' (substantially identical with respect to parallel set of beams of radiation 14) may also be projected from a symmetrical position with respect to instrument axis 51.

As shown in FIG. 1, camera 50 (preferably a CCD camera which is well known to those of ordinary skill in the art) is positioned to view cornea 31 along instrument axis 51 to record traces of set of beams 14 and/or 14' scattered by cornea 31. Instrument axis 51 is aligned with a visual axis of eye 30 in accordance with any one of a number of methods and mechanisms which are well known to those of ordinary skill in the art (such mechanisms are not shown for clarity and ease of understanding the principles of present invention). Although CCD camera 50 is shown to be physically disposed along instrument axis 51, it should be appreciated by those of ordinary skill in the art that CCD camera 50 may be aligned at other positions. In that case, optical systems which are well known to those of ordinary skill in the art (for example, beam splitting systems) should be used to ensure that camera 50 records images as if it were disposed as shown in FIG. 1.

A rotation mechanism, not shown in FIG. 1 for ease of understanding the principles of the present invention, rotates radiation assembly 10 and optical plate assembly 20 which produce parallel beams 14 (and radiation assembly 10' and optical plate assembly 20' which produce parallel beams 14') about instrument axis 51. As a result, and in accordance with the present invention, a trace of each of the beams comprising set of beams 14 (and set 14') forms a thin conical sheet in space.

Figure 2:
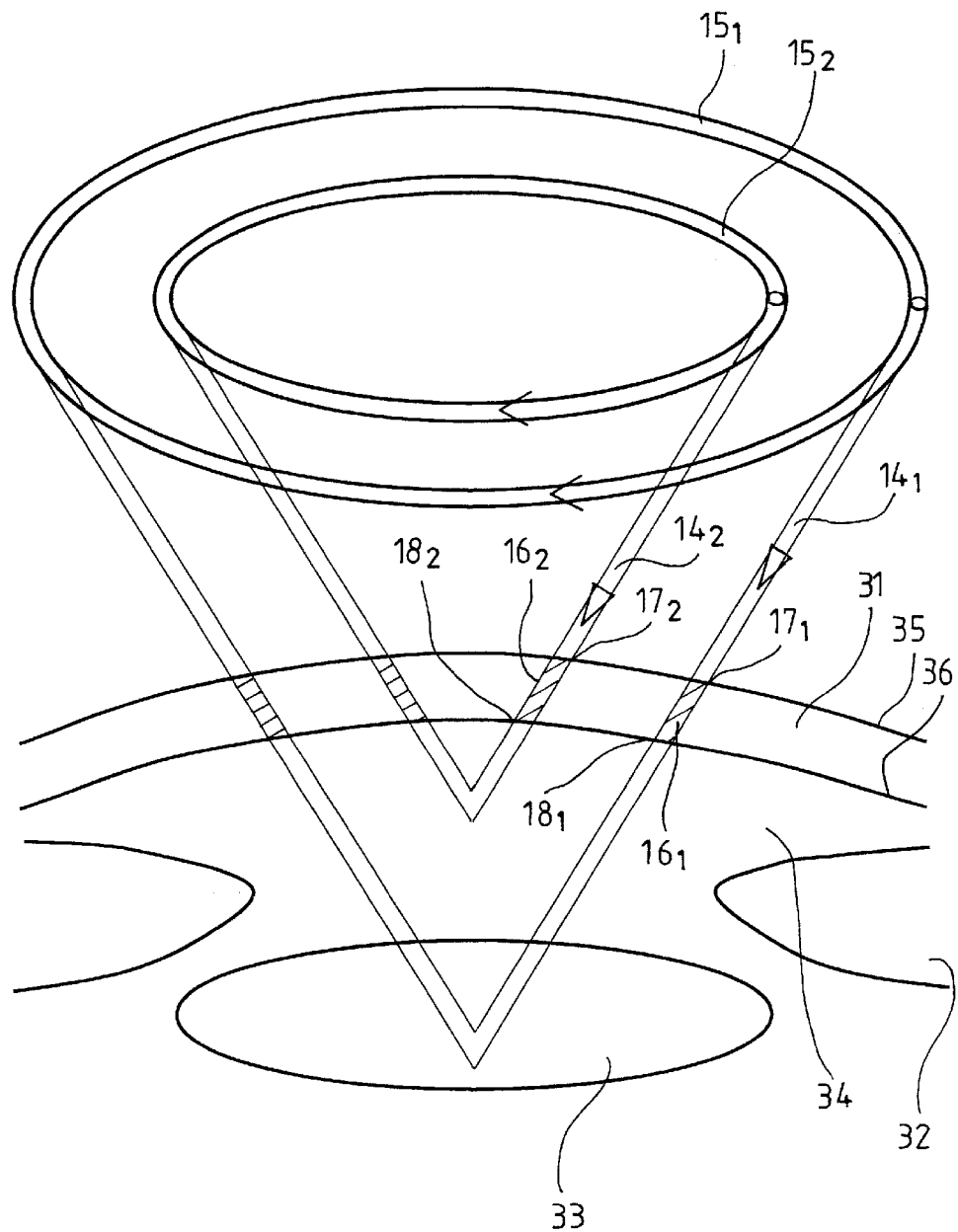
FIG. 2 shows, in pictorial form, traces of rotationally scanning, beams intersecting with a cornea.

FIG. 2 shows, in pictorial form, traces of rotationally scanning set of beams 14 (in particular beams $14_1$ and $14_2$) that intersect cornea 31. A trace of each beam in set of beams 14 is a thin, conical sheet, as illustrated by conical sheets $15_1$ and $152_2$, respectively. Intersection traces $16_1$ and $16_2$ on cornea 31 resulting from conical sheets $15_1$ and $15_2$, respectively, form a set of rings. As is well known to those of ordinary skill in the art, stroma which comprise cornea 31 scatter radiation much more strongly than does lens 33 of eye 30 or liquid in anterior chamber 34 of eye 30, i.e., the aqueous humor. As a result, images of intersection traces $16_1$ and $16_2$ in CCD camera 50 form a set of bright rings. The outer edges of the rings correspond to intersections between anterior surface 35 of cornea 31 and conical sheets $15_1$ and $15_2$, i.e., points $17_1$ and $17_2$, respectively, shown in FIG. 2. Likewise, the inner edges of the rings correspond to intersections between posterior surface 36 of cornea 31 and conical sheets $15_1$ and $15_2$, i.e., points $18_1$ and $18_2$, respectively, shown in FIG. 2.

In accordance with the present invention, CCD camera 50 records images of the rings formed from intersection traces $16_1$ and $16_2$, one picture per rotation (or one picture per half rotation if identical set of beams 14' is also used). The recording is synchronized with rotation of set of beams 14 in accordance with any one of a number of methods that are well known to those of ordinary skill in the art. For example, signals are transmitted from motor 43 shown in FIG. 3 to controller 60 (for example, computer 60) shown in FIG. 1 to synchronize the timing of CCD camera 50. When the beams in set of beams 14 are appropriately spaced, the rings formed in the images obtained from CCD camera 50 are separated and approximately concentric. The space between the beams in set of beams 14 depends on the thickness of optical plate 20, the angle at which beam of radiation 13 impinges upon surface 21, and so forth. The details of the sizes and shapes of the rings in the images depend on the position and contour profile of cornea 31.

Computer 60, shown in FIG. 1, analyzes data provided by the ring images from CCD camera 50. For example, in accordance with any one of a number of methods that are well known to those of ordinary skill in the art, the CCD image is digitized (the digitized image can be stored), and the pixels are examined and quantified for brightness information. Then, in accordance with any one of a number algorithms that are well known to those of ordinary skill in the art, data points along the outer and inner edges of the image rings are identified, respectively, with the anterior and posterior surfaces of cornea 31. These data points can then be analyzed to reconstruct the corneal profile.

First, based on well known triangulation algorithms, the longitudinal position of cornea 31 (i.e., position along instrument axis 51) can be determined by the size of the center ring. In this respect, the size of the center ring can also be used for longitudinal alignment purposes. As shown in FIG. 2, the longitudinal position of the tip of each conical sheet can be predetermined. Further, the size of the center ring is proportional to the distance of cornea 31 from the tip of the innermost conical sheet.

Second, the contour of anterior surface 35 of cornea 31 can be determined from the outer edges 17 of the bright ring images. The spatial positions of data points along the outer edges of the rings are calculated using a direct triangulation algorithm which is well known to those of ordinary skill in the art. These data points are then used in accordance with methods that are well known to those of ordinary skill in the art to reconstruct the anterior surface profile of cornea 31.

Third, given the anterior surface profile of cornea 31, a ray tracing triangulation algorithm which is well known to those of ordinary skill in the art is used to determine spatial positions of data points along the inner edges of the rings. These data points are then used in accordance with methods that are well known to those of ordinary skill in the art to reconstruct the posterior surface profile of cornea 31.

Finally, the thickness profile of cornea 31 is determined by spatial differences between the contour profiles of anterior surface 35 and posterior surface 36 of cornea 31. Algorithms for use in determining anterior surface 35 and posterior surface 36 of cornea 31 can be, in principle, similar to that disclosed in U.S. Pat. No. 5,512,966, which is discussed in the Background of the Invention. The computer calculation, however, can be significantly simplified for the present invention because all the data points along a given ring have a similar viewing angle from the camera. In comparison, the data points along a given slit image have a different viewing angle from point to point.

In accordance with a preferred embodiment of the present invention, each beam of set of beams 14 has a spot size of about 100 microns. This spot size corresponds to a confocal length of about 4 cm at a near infrared wavelength (for a laser beam, the spot size remains substantially unchanged within its confocal length). Such narrow and substantially collimated beams lead to sharp, bright ring images, and thus enable an accurate reconstruction of anterior surface 35 and posterior surface 36 of cornea 31.

In comparison, the slit beam method and apparatus of the Snook patents produce a beam that is less collimated and has a width of about 800 microns on cornea 31. Uncertainty of beam width across cornea 31 leads to uncertainty in reconstruction of posterior surface 36, and hence, to uncertainty in reconstruction of the thickness profile of cornea 31.

In accordance with the present invention, in order to provide more bright ring images while keeping the rings separate from one another, several pictures may be needed with a small displacement of the beams which comprise set of beams 14 (and 14') from picture to picture. One simple method of generating the displacement is to translate longitudinally the rotation stage with all the beams, one small step for each picture.

Although FIG. I shows set of beams 14' being substantially identical to set of beams 14, the present invention is not limited to such a configuration. It is within the spirit of the present invention for sets of beams 14 and 14' to impinge at different locations on cornea 31 and even at different angles with respect to instrument axis 51. Further, the number of beams in each set may differ. For example, the number of beams in either or both of sets of beams 14 and 14' may be as little as one.

Figure 3:
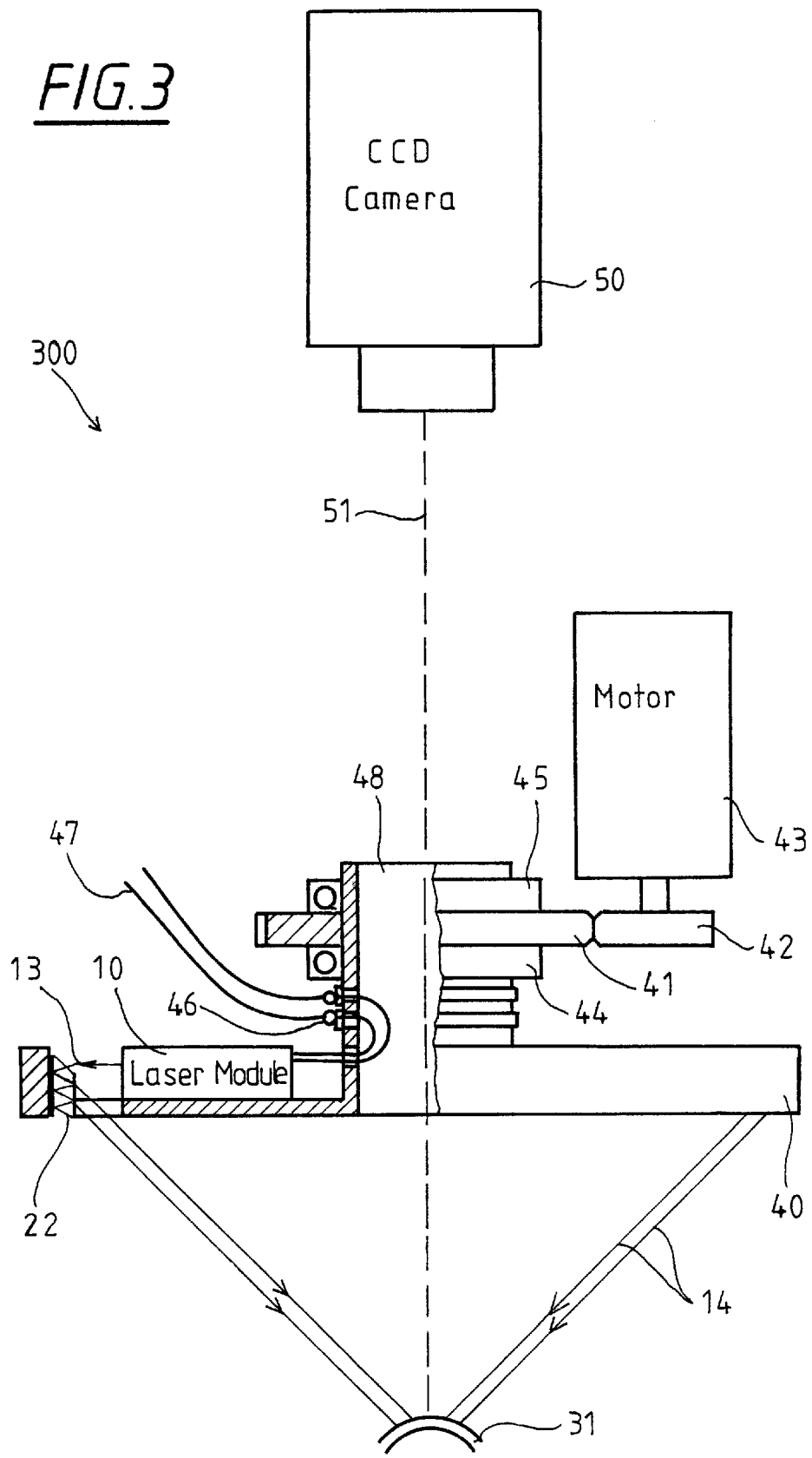
FIG. 3 shows a diagram of an embodiment of the present invention.

FIG. 3 shows a diagram of embodiment 300 of the present invention. As shown in FIG. 3, laser module system 10 produces collimated infrared beam 13 which is directed to impinge upon optical plate 22 to generate a set of substantially parallel beams 14. As further shown in FIG. 3, set of beams 14 is projected onto cornea 31.

As shown in FIG. 3, laser module system 10 and optical plate 22 are mounted on rotational stage 40 that is supported by a pair of bearings 44 and 45. The left half of stage 40 is a cross sectional diagram to illustrate the detail of rotational stage 40. Motor 43 drives rotational stage 40 through gears 41 and 42 to rotate around instrument rotation axis 51 in response to signals sent from computer 60 over lines that are not shown for clarity. A set of slip ring electrodes 46 couple electrical power from a source (not shown) to laser module assembly 10 through leads 47.

As further shown in FIG. 3, CCD camera 50 is located to view along instrument rotation axis 51. Rotation stage 40 includes opening 48 along instrument rotation axis 51 to provide a viewing access for CCD camera 50.

As was discussed above, the inventive apparatus includes a fixation device which engages the attention of a measured eye and which may be fabricated in accordance with any one of a number of methods that are well known to those of ordinary skill in the art. For example, a fixation device may include an LED that is disposed at a predetermined location for viewing by the patient's measured eye.

Figure 4:
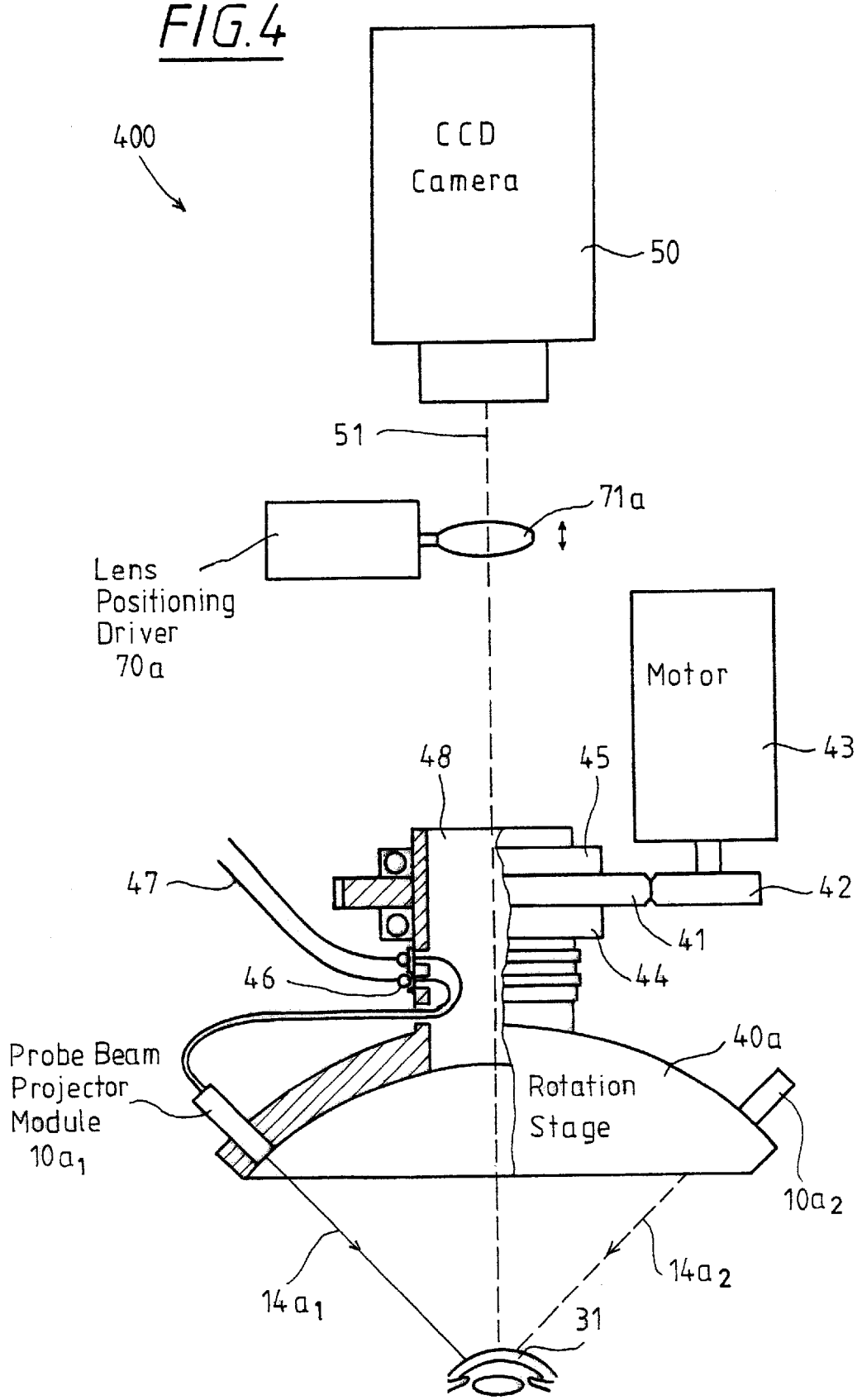
FIG. 4 shows a diagram of an alternative embodiment of the present invention.

FIG. 4 shows alternative embodiment 400 of the present invention. Embodiment 400 is a modification of embodiment 300 to implement a near confocal image configuration. In alternative embodiment 400, a set of probe beam projector modules 10a is installed around a circle on a rotational stage 40a and projects a set of probe beams 14a onto cornea 31. For illustrative purposes, FIG. 4 shows only two of the set of projector modules $10a_1$ and $10a_2$ and their corresponding probe beams $14a_1$ and $14a_2$, respectively. In a preferred embodiment, each of the beams of set of probe beams 14a intersects instrument axis 51 at the same angle, but at a slightly different height along instrument axis 51. Further, each of the beams of set of probe beams 14a is aligned to focus on cornea 31.

In operation, rotational stage 40a rotates continuously and probe beam projector modules 10 are energized, one at a time, in a predetermined sequence to produce the beams in set of beams 14a. CCD camera 50, rotational stage 40a, and the energizing of probe beam projector modules 10a are synchronized so that only a single ring image is captured in each frame acquired by CCD camera 50. Meanwhile, optical focusing system positioning driver 70a fine tunes the longitudinal position of optical focusing system 71a (for example, a focal lens) to ensure that CCD camera 50 is confocal with respect to the particular probe beam that has been projected. In this manner, near confocal imaging can be obtained over all the rings, and sharper images can be achieved. Although optical focusing system 71 a and optical focusing system-positioning driver 70a are shown as separate from CCD camera 50 and the lower stages of embodiment 400 in FIG. 4, those of ordinary skill in the art can readily appreciate that these components can be fabricated as part of either CCD camera 50 or the lower stages of embodiment 400 or distributed as a part of both.

Alternative embodiment 400 acquires one image ring per frame and, hence, requires a longer data acquisition time than does embodiment 300 shown in FIG. 1. However, in accordance with alternative embodiment 400 of the present invention, one obtains better image quality, and a non-coherent light source may be used for the probe beams (i.e., a near confocal imaging configuration reduces the restriction on confocal length of the beams of set of probe beams 14*a*). Further, set of probe beams 14*a* can be aligned independently, and can be turned away slightly from instrument axis 51 to avoid specular reflection into CCD camera 50.

Figure 5:
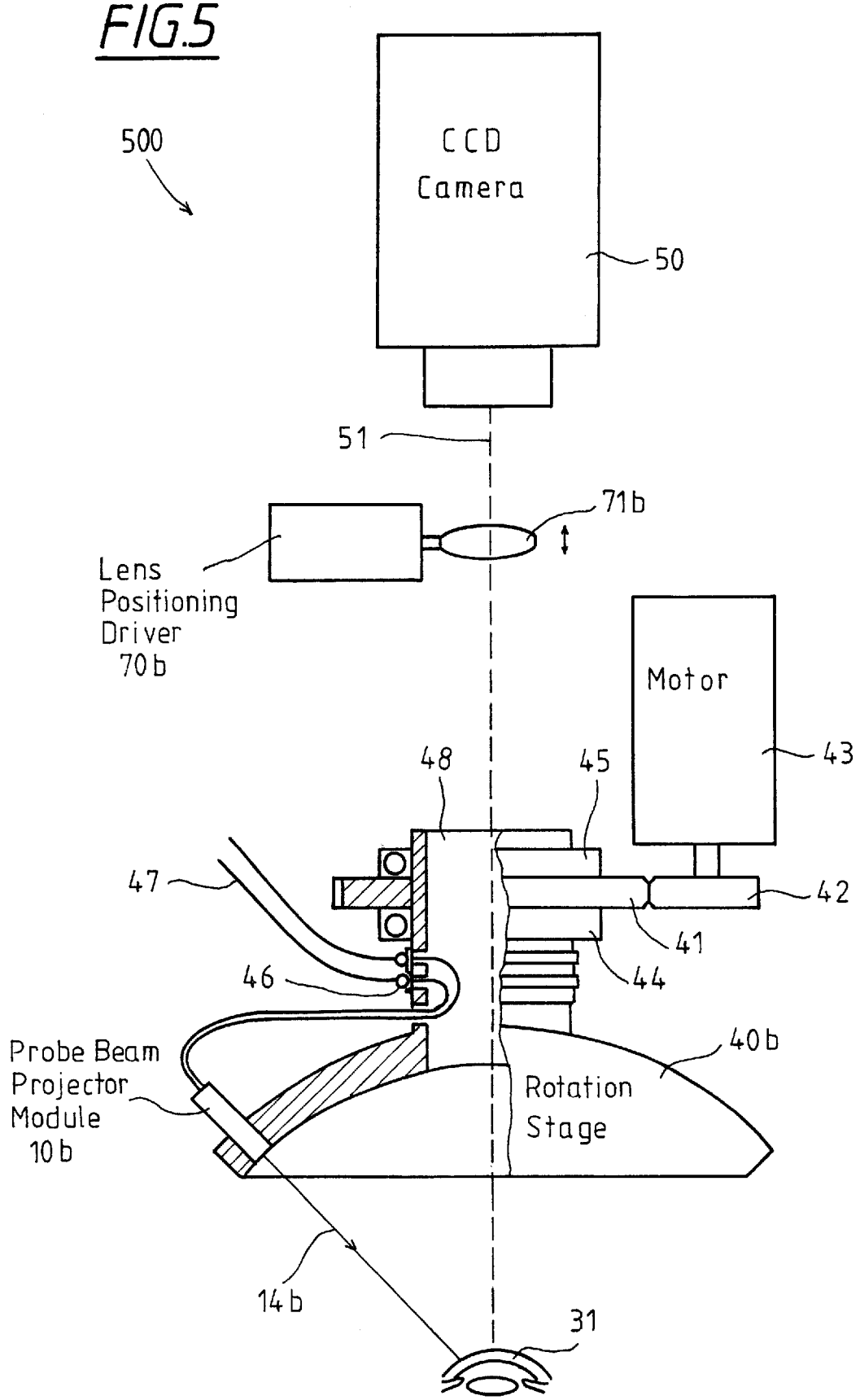
FIG. 5 shows a diagram of a variation of the alternative embodiment shown in FIG. 4.

FIG. 5 shows further alternative embodiment 500 which is a modification of embodiment 400 shown in FIG. 4. As shown in FIG. 5, one probe beam projector module 10*b* is used to project single probe beam 14*b*, which probe beam 14*b* is focused on cornea 31. In operation, probe beam projector module 10*b* is rotated with rotational stage 40*b*, and a single ring image is formed in each frame acquired by CCD camera 50. A displacement mechanism, which is not shown in FIG. 5, displaces probe beam 14*b* in a predetermined manner so that probe beam 14*b* impinges at displaced positions across cornea 31 to form a sequence of rings in a corresponding sequence of frames acquired by CCD camera 50. One way, as an example, to displace probe beam 14*b* is to translate rotational stage 40*b* as a unit along instrument axis 51.

In operation, rotational stage 40*b* rotates continuously, and probe beam 14*b* is displaced in a predetermined manner. CCD camera 50, rotational stage 40*b*, and the displacement of probe beam 14*b* are synchronized so that only a single ring image is captured in each frame acquired by CCD camera 50. Meanwhile, optical focusing system positioning driver 70*b* fine-tunes the longitudinal position of optical focusing system 71*b* (for example, a focal lens) to ensure that CCD camera 50 is confocal with respect to probe beam 14*b*. Thus, near confocal imaging can be obtained for all the rings, and sharper images can be achieved. Although optical focusing system 71*b* and optical focusing system-positioning driver 70*b* are shown as separate from CCD camera 50 and the lower stages of embodiment 500 in FIG. 5, those of ordinary skill in the art can readily appreciate that these components can be fabricated as part of either CCD camera 50 or the lower stages of embodiment 500 or distributed as a part of both.

The corneal contours and thickness profile can be reconstructed using the imaged rings acquired in embodiments 400 or 500 in a similar manner as that described above in conjunction with embodiment 300 shown in FIG. 3.

Those skilled in the art will recognize that the foregoing description has been presented for the sake of illustration and description only. As such, it is not intended to be exhaustive or to limit the invention to the precise form disclosed.

What is claimed is:

1. An apparatus for mapping a corneal contour and thickness profile of a patient's eye which comprises:
    a source which projects a set of beams of radiation onto a cornea of the patient's eye;
    a rotator which rotates the source;
    a camera which acquires images of radiation scattered by the cornea; and
    a controller which analyzes the images to construct the corneal contour and thickness profile.

2. The apparatus of claim 1 wherein the source comprises a radiation source that applies radiation output therefrom to an optical plate.

3. The apparatus of claim 2 wherein the optical plate includes a first and a second surface that are substantially parallel wherein the first surface is substantially totally reflecting to the radiation and the second surface is partially reflecting to the radiation.

4. The apparatus of claim 3 wherein the source comprises a laser diode.

5. The apparatus of claim 2 wherein the radiation output is substantially collimated.

6. The apparatus of claim 5 wherein the radiation has a wavelength substantially in a range from about 700 nm to about 1300 nm.

7. The apparatus of claim 1 wherein the camera is a CCD camera.

8. The apparatus of claim 1 wherein the beams impinge upon the cornea at a predetermined angle with respect to a optical axis of the camera.

9. The apparatus of claim 1 wherein the source comprises a set of beam projectors.

10. The apparatus of claim 9 wherein set of beam projectors focus the beams of radiation on the cornea.

11. The apparatus of claim 9 which further comprises an optical focusing system disposed to provide near confocal imaging of the radiation scattered by the cornea.

12. The apparatus of claim 11 wherein the optical focusing system is displaceable and the apparatus further comprises an optical focusing system positioning driver which displaces the optical focusing system to provide the near confocal imaginig in a predetermined time sequence.

13. The apparatus of claim 9 wherein the probe beam are of non-coherent radiation.

14. A method for mapping a corneal contour and thickness profile of a patient's eye which comprises the steps of:
    projecting a set of beams of radiation onto a cornea of the patient's eye;
    rotating the set of beams;
    acquiring images of radiation scattered by the cornea; and
    analyzing the images to construct the corneal contour and thickness profile.

15. The method of claim 14 wherein the step of projecting comprises projecting from a set of beam projectors.

16. The method of claim 15 wherein acquiring-images comprises near confocal imaging of the radiation scattered by the cornea.

17. The method of claim 16 wherein probe beams comprise non-coherent radiation.

18. An apparatus for mapping a corneal contour and thickness profile of a patient's eye which comprises:
    a source which projects a beam of radiation onto a cornea of the patient's eye;
    a rotator which rotates the source;
    a displacement mechanism which displaces the source;
    a camera which acquires images of radiation scattered by the cornea at various displacements of the source;
    a controller which analyzes the images to construct the corneal contour and thickness profile.

19. The apparatus of claim 18 which further comprises an optical focusing system disposed to provide near confocal imaging of the radiation scattered by the cornea.

20. The apparatus of claim 19 wherein the optical focusing system is displaceable to provide the near confocal imaging at predetermined displacements of the source.

21. The apparatus of claim 20 which further comprises an optical focusing system positioning driver which displaces the optical focusing system.

22. The apparatus of claim 19 wherein the source is source of non-coherent radiation.

23. A method for mapping a corneal contour and thickness profile of a patient's eye which comprises:
    projecting a beam of radiation onto a cornea of the patient's eye;

rotating the beam of radiation;

displacing the beam of radiation;

acquiring images of radiation scattered by the cornea at various displacements of the beam; and analyzing the images to construct the corneal contour and thickness profile.

24. The method of claim 23 wherein acquiring-images comprises a near confocal imaging of the radiation scattered by the cornea.

25. The method of claim 24 wherein the beam is a non-coherent beam of radiation.

* * * * *